United States Patent
Savage et al.

(10) Patent No.: US 7,445,703 B2
(45) Date of Patent: Nov. 4, 2008

(54) WATER CONDUCTIVITY MONITORING CIRCUIT FOR USE WITH A STEAM GENERATOR

(75) Inventors: Jason Randall Savage, St. Joseph, MI (US); Dwain Francis Moore, Benton Harbor, MI (US); Thomas N. Robinson, Grand Rapids, MI (US); Joel Matthew Sells, Hartford, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 223 days.

(21) Appl. No.: 11/366,797

(22) Filed: Mar. 1, 2006

(65) Prior Publication Data

US 2007/0205160 A1    Sep. 6, 2007

(51) Int. Cl.
*B01D 35/143* (2006.01)
*B01D 35/00* (2006.01)
(52) U.S. Cl. ............... 210/85; 210/749; 210/748; 210/746
(58) Field of Classification Search ............ 210/746, 210/85, 749, 748
See application file for complete search history.

(56) References Cited

U.S. PATENT DOCUMENTS

| 3,814,901 | A | 6/1974 | Morhack | 219/401 |
| 3,919,627 | A | 11/1975 | Allen | 324/30 |
| 4,496,906 | A | 1/1985 | Clack | 324/439 |
| 4,806,912 | A | 2/1989 | Clack | 340/603 |
| 5,178,125 | A | 1/1993 | Kuen | 126/20.2 |
| 6,078,178 | A | 6/2000 | Barnett | 324/439 |
| 6,217,751 | B1 * | 4/2001 | Peeters | 210/85 |

* cited by examiner

*Primary Examiner*—Walter D. Griffin
*Assistant Examiner*—Cameron J Allen
(74) *Attorney, Agent, or Firm*—John Morrison; Michael D. LaFrenz

(57) ABSTRACT

A water conductivity monitoring circuit determines the status of an ion exchange filter in the water flow to a steam generator. A microprocessor sends a reference signal to a conductivity sensor circuit that converts it to an excite signal that is sent to a probe in the water flow. Any conductivity of the water alters the excite signal, and the modified signal is compared to the reference signal to establish a value indicative of the conductivity of the water. The microprocessor compares the value to at least two thresholds representative of the status of the filter.

14 Claims, 7 Drawing Sheets

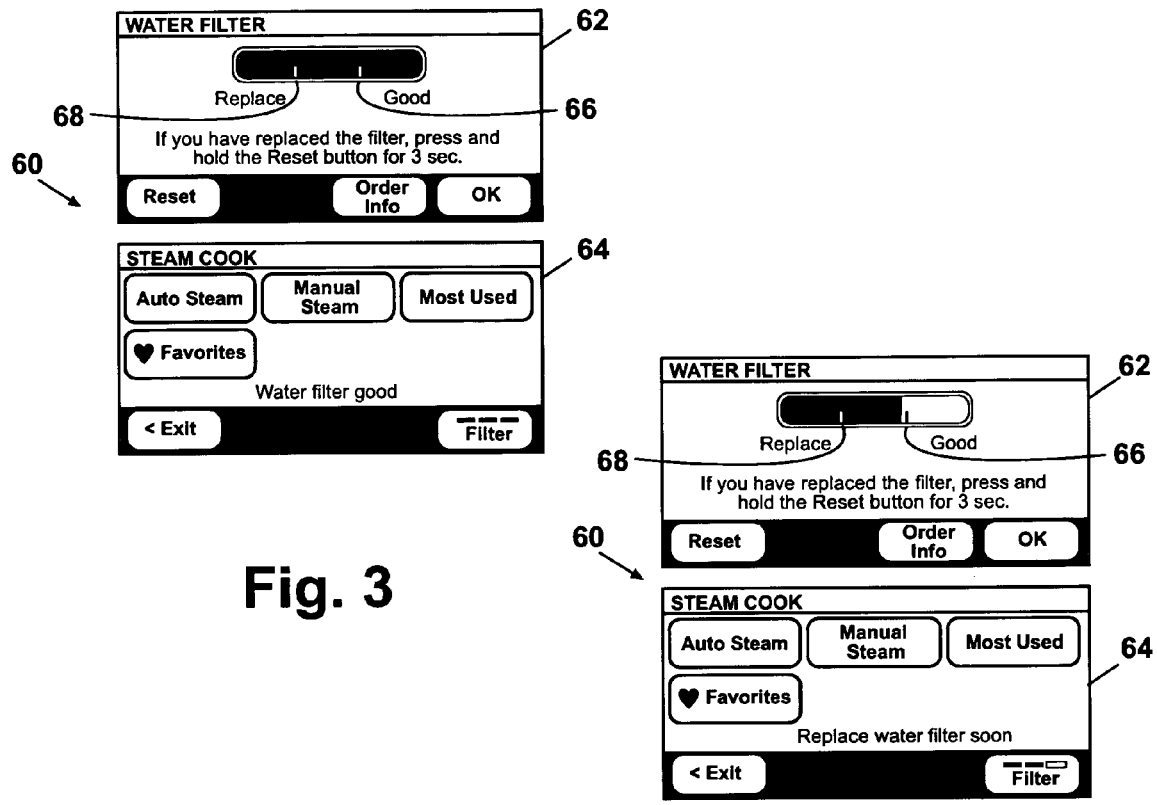
Fig. 3
Fig. 4
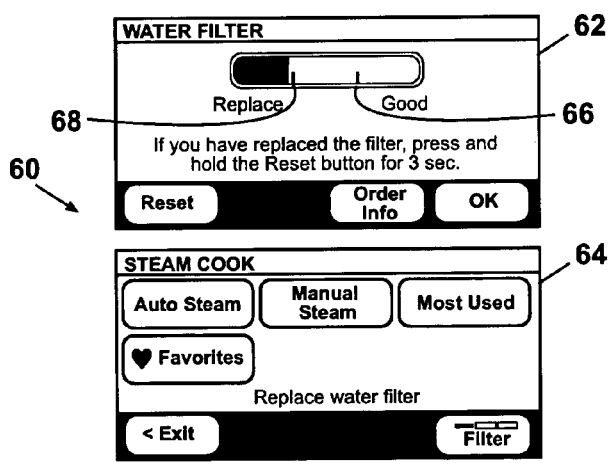
Fig. 5

WATER CONDUCTIVITY MONITORING CIRCUIT FOR USE WITH A STEAM GENERATOR

BACKGROUND OF THE INVENTION

1. Field of the Invention

The invention relates generally to water conductivity monitoring circuits and, more particularly, to a circuit that uses a microprocessor for monitoring water conductivity in a steam generator.

2. Description of the Related Art

Steam generation is found in home appliances for a variety of different uses. For example, it is known to use a steam generator in an oven for cooking applications. In a steam generator, a water source typically supplies water to a boiler to generate steam. For a steam generator in an oven, water can be supplied from a reservoir and pumped into the boiler, or directly from a continuously pressurized water source such as a municipal water supply.

Most common sources of water leave calcium and magnesium deposits in the boiler after the water is vaporized into steam, a cumulative build up of which adversely affects performance. One solution to the build up of deposits in a boiler is to add a cleaning solution to the water source that will dissolve the deposits, and then flush the effluent through a drain. A more common and practical solution in home appliances is to limit the dissolved solids that can reach the boiler by using an ion exchange filter upstream of the boiler. An ion exchange filter typically removes 99% of all dissolved solids from the source water, leaving essentially pure water for steam generation in the boiler.

The principal problem with a filter, however, is that it must be replaced periodically when it becomes saturated with solids or when it otherwise breaks down and its usefulness expires. There is a need to determine when to replace a filter in a steam generator.

It is known to measure the purity of water by measuring its conductivity value, since the conductivity of water is directly proportional to the quantity of ionizable dissolved solids found in the water. U.S. Pat. No. 4,496,906 to Clack discloses a device for continuously monitoring the electrical conductivity of a liquid. The device includes a housing with parallel-spaced electrodes for insertion into a liquid, and a transparent user-viewable lens. The electrodes are connected within the housing to a differential amplifier which provides a change in output signal level when the liquid conductivity exceeds a predetermined threshold level. A pair of LED's of different colors connected between respective unidirectional current sources from the output of the differential amplifier and viewable through the lens indicate acceptable and unacceptable conductivity levels of the water.

But, assessing the purity of water by measuring conductivity carries its own set of problems. For example, introducing an electrical current from a probe changes the very chemistry of the water to be measured. As well, probes get contaminated with deposits that affect their sensitivity. Further, known water purity conductivity devices provide only a "thumbs up" or thumbs down" assessment, measured against a fixed threshold. Either the water meets a standard of purity or it does not.

SUMMARY OF THE INVENTION

These and other known limitations of the prior art are resolved in the present invention of a water conductivity monitoring circuit for a steam generator for determining the status of a water filter disposed in water flow upstream from a steam generator. The circuit includes a microprocessor for generating a reference signal, a probe adapted to be positioned in the water flow downstream from the filter, and a conductivity sensor circuit intermediate the microprocessor and the probe for outputting to the microprocessor an output signal indicative of the conductivity of the water. When the probe is positioned in the water flow, the microprocessor can assess the status of the filter based on a comparison of the reference signal to the output signal.

A display can be connected to the microprocessor to show the status of the filter visually. Preferably, the circuit includes at least two threshold levels against which the comparison can be measured, one of which indicates a need to change the filter. In one embodiment, a warning threshold is set at a conductivity of about 50 µS/cm, and a change threshold is set at about 100 µS/cm.

Typically, the reference signal will be a pulsed wave, and the conductivity sensor circuit can include means to convert the reference signal to an excite signal to be sent to the probe. Preferably, the reference signal is in a range of 1-10 volts.

The probe can have two electrodes, one of which is connected to ground. As well, the circuit can include means to purge the water flow after changing the filter, in which case, the output signal is overridden for a predetermined time.

In another aspect of the invention, a method of determining the status of a water filter disposed in water flow upstream from a steam generator includes the steps of providing a microprocessor, a probe positioned in the water flow downstream from the filter, and a conductivity sensor circuit intermediate the microprocessor and the probe, generating a reference signal from the microprocessor by way of the conductivity sensor circuit to the probe, sending an output signal from the probe to the microprocessor by way of the conductivity sensor circuit, comparing the reference signal to the output signal to determine a value, and comparing the value to a predetermined threshold level representative of the status of the filter. Preferably, the reference signal will be a pulsed square wave.

The method can include the step of sending a display signal to a visual display indicative of the status of the filter. Preferably, the method includes least two thresholds, one of which indicates a need to change the filter. In one embodiment, a warning threshold is set at a conductivity of about 50 µS/cm, and a change threshold is set at about 100 µS/cm.

As well, the method can include the step of converting the reference signal to an excite signal that is sent to the probe by the conductivity sensor circuit. Also, it can include the step of purging the water flow if the filter is changed. In addition, it can include the step of applying a voltage divider to any of the signals to control the maximum voltage level. A preferred method will keep the reference signal in a range of 1-10 volts.

BRIEF DESCRIPTION OF THE DRAWINGS

In the drawings:

FIG. 3 is an exemplary display to the user showing the filter in good condition.

FIG. 4 is an exemplary display to the user showing the filter approaching the time for replacement.

FIG. 5 is an exemplary display to the user showing the filter needs replacement.

DETAILED DESCRIPTION

Figure 1:
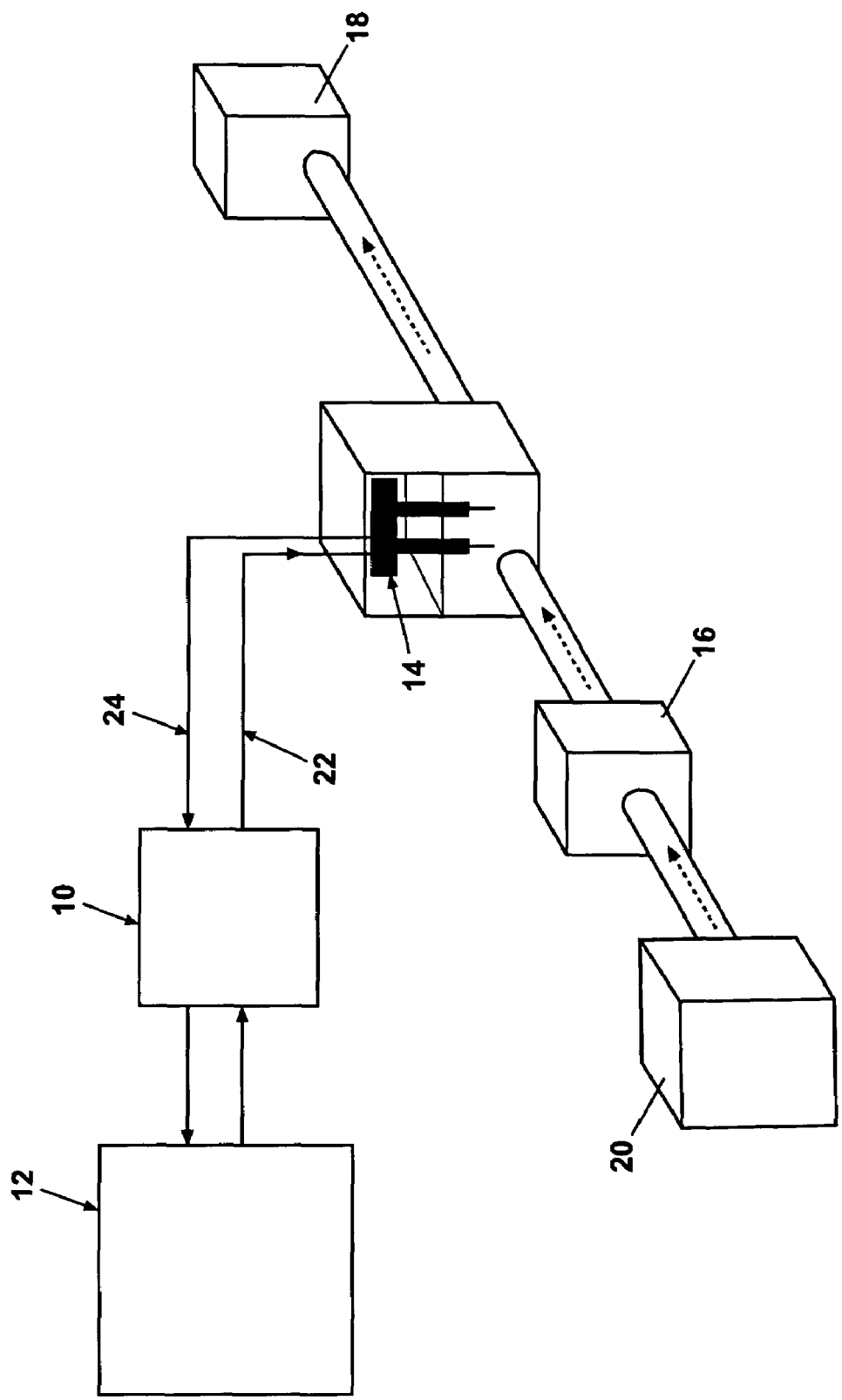
FIG. 1 is a schematic diagram showing a water monitoring circuit according to the invention.

Looking first at FIG. 1, a water monitoring circuit according to the invention utilizes a conductivity sensor circuit 10 in conjunction with a microprocessor 12 to evaluate signals sent through a probe 14 positioned in water flow downstream from an water filter 16, and upstream from a steam generator 18 in a home appliance. For this embodiment, the home appliance is considered to be an oven and the water filter is an ion exchange filter. Water from a water source 20 flows through the ion exchange water filter 16, past the probe 14, to the steam generator 18 where steam is produced and introduced into the oven in a manner well-known in the art. The particular type of steam generator and filter used is not important to invention. Generally, the microprocessor 12, preferably in an electronic oven control, generates a reference or input signal that goes into the conductivity sensor circuit 10 and then to the probe 14. The input signal is modified by the water at the probe and then goes back through the conductivity sensor circuit 10 and to the microprocessor 12 as an output signal. The microprocessor 12 compares the reference signal to the output signal, which is influenced by the water, to assess the conductivity of the water and determine the status of the filter based on the assessment. While the filter is good the conductivity of the water is very low. When the filter starts to break down the conductivity will go up, and once some threshold is reached, the filter needs to be changed.

Figure 2:
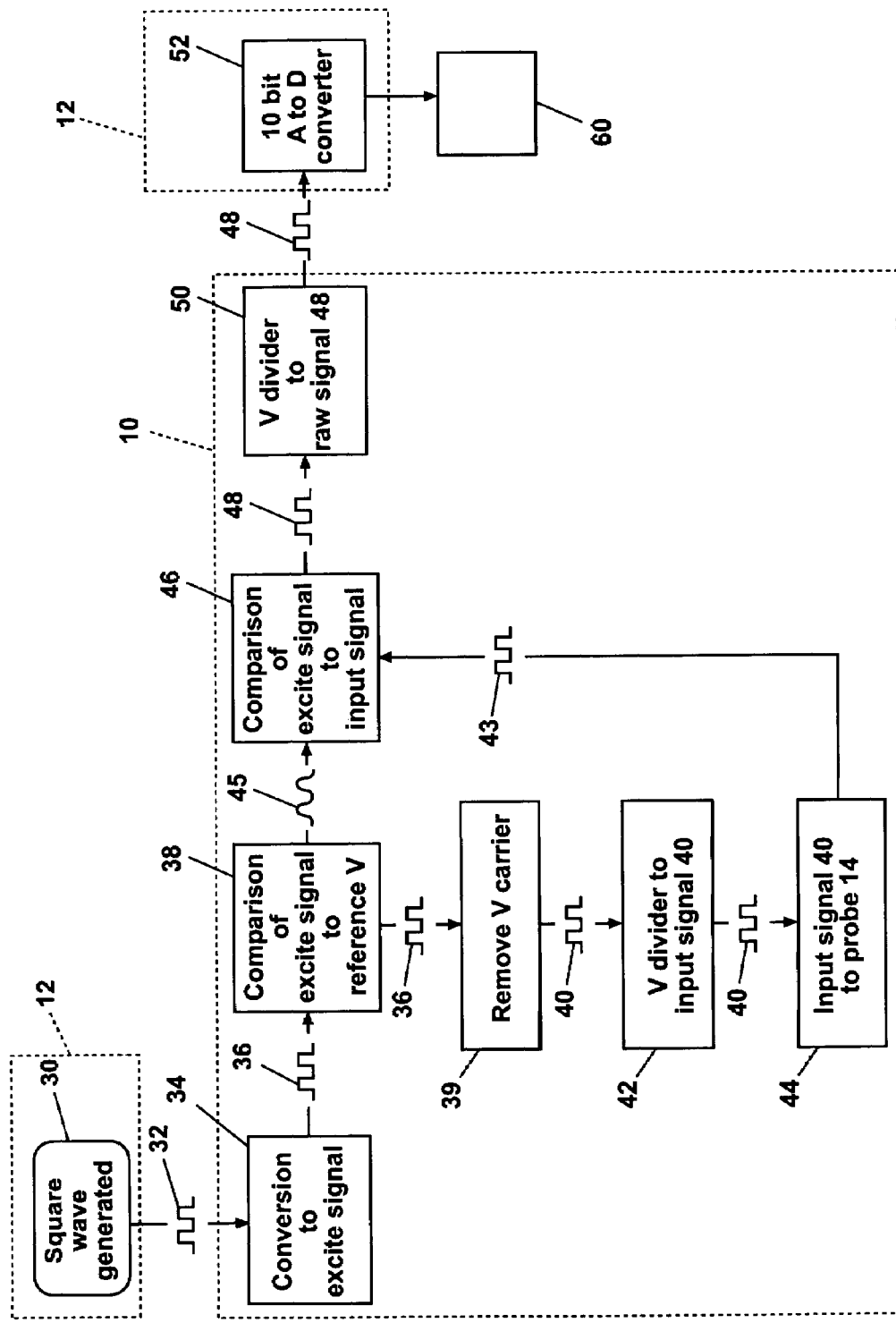
FIG. 2 is a flow chart showing the process for monitoring water conductivity according the invention.

The process is better illustrated in the flow chart of FIG. 2. At block 30, the microprocessor 12 generates a pulse train, i.e., an original square wave signal 32 of up to 5 volts at a frequency of 1 KHz, for example. Lower voltages can be used at higher frequencies. An appropriate range of frequencies is from 1-10 KHz. For example, at 5 KHz, one would likely use a voltage of 3.3V. Frequencies higher than 10 KHz are less useful because higher frequencies tend to change the chemistry of the water being monitored.

From the microprocessor 12, the original square wave signal 32 is sent to the conductivity sensor circuit 10 where at block 34 it is converted into an excite signal 36. The excite signal 36 is a signal that is preferably +/−100 mv on a 6V DC carrier. If the original square wave signal 32 is 3.3V at 5 KHz, then the excite signal 36 will be +/−300 mv. At block 38, the conductivity sensor circuit 10 uses a differential amplifier to compare the excite signal 36 to a 6V DC reference, sending the excite signal 36 one way and a comparison output signal 45 another way. At block 39, a capacitor removes the 6V DC carrier from the excite signal 36 to form an input signal 40. A voltage divider can be applied to the input signal 40 at block 42 before going to the probe, if desired, to reduce the voltage of the input signal 40. The input signal 40 is then sent to one electrode of the probe 14 at block 44 where it may be modified by the water to an output signal 43.

At block 46, the output signal 43 at the probe 14 (the input signal as modified by the water) is compared at a second differential amplifier to the comparison output signal 45 of the first differential amplifier and outputs a raw final signal 48. At block 50, a voltage divider is applied to the raw final signal 48 to insure that the maximum voltage is ready for the microprocessor 12, preferably not exceeding 5 V. At block 52, the reduced raw final signal 48 is measured with a 10 bit analog to digital converter in the microprocessor 12 which reads the level in counts where 1 count=3.2 mv for maximum 3.3V input. The microprocessor 12 then compares the count level to a pre-loaded threshold and sends a display signal indicative of the water conductivity to a display 60 from which the status of the filter can be seen.

FIG. 3 shows a display 60 where the signal from the microprocessor 12 indicates that the filter is in good condition. The display 60 includes a filter display 62 and a steam cook display 64. The filter display 62 includes two thresholds for the status of the filter, a first threshold 66 where the measured conductivity is about 50 μS/cm, and second threshold 68 where the measured conductivity is about 100 μS/cm. At least two thresholds will provide basic information on the status of the filter. The first threshold 66 is a warning threshold indicating that the filter 16 has to be changed soon, as shown in FIG. 4. While the water conductivity is below the first threshold 66, the filter status will be good and no recommendation will be provided to the user.

FIG. 4 shows the display 60 where the signal from the microprocessor 12 indicates that the filter needs to be replaced soon. While the value is above the first threshold 66 and below the second threshold 68, the user will be warned that the time to change the filter will come soon.

FIG. 5 shows the display 60 when the second threshold 68 has been reached. The second threshold 68 is a change threshold indicating that the filter has to be changed now. If the detected water conductivity level is above the second threshold 68, the steam cook display 64 will ask the user to change the filter. More thresholds can be used if finer resolution of the filter status is desired.

Figure 6:
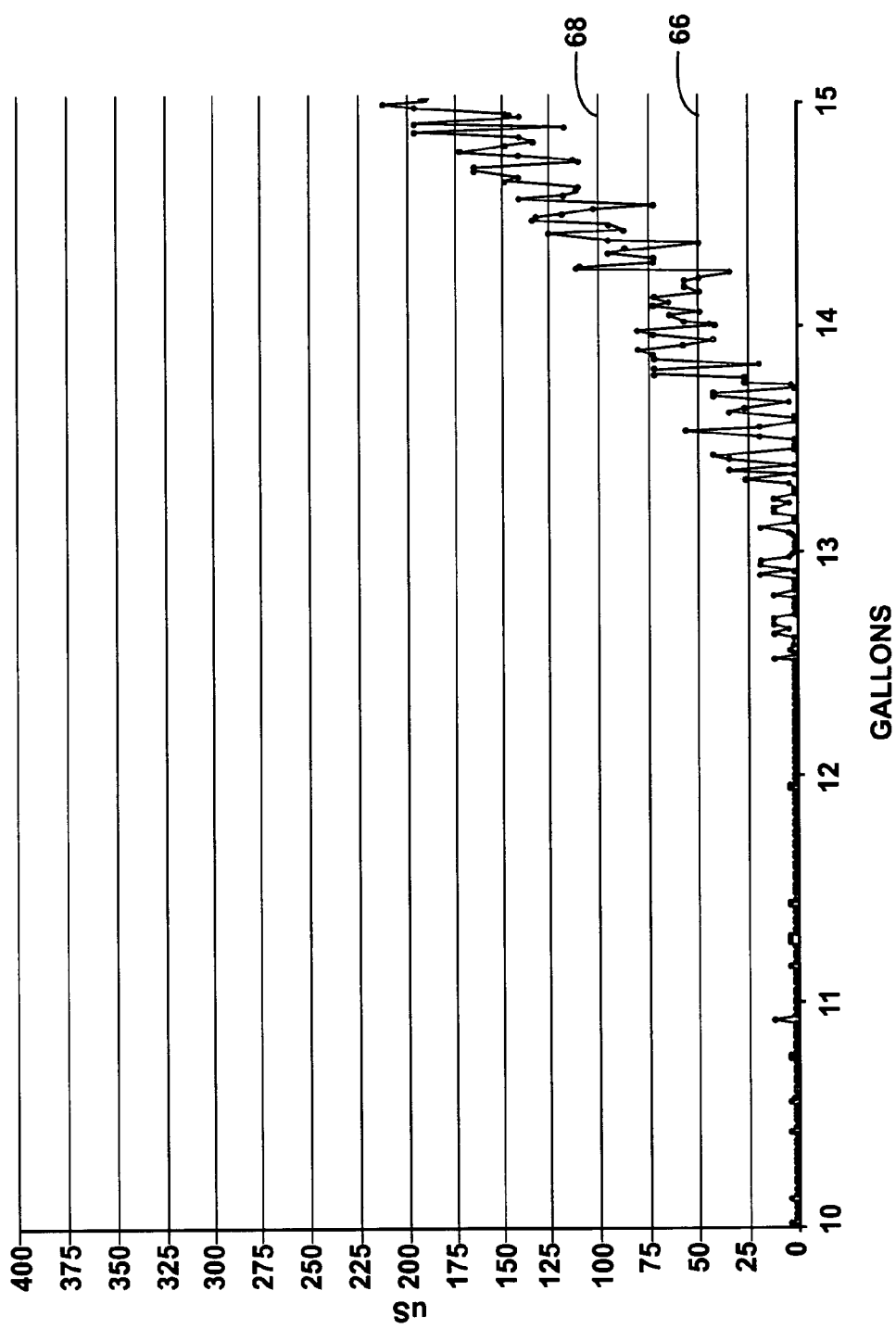
FIG. 6 is chart plotting conductivity of the cumulative amount of water going through the filter.

One can see from FIG. 6 that as more water goes through the filter, conductivity of the water downstream from the filter begins to increase at some point. The thresholds 66, 68 are predetermined empirically to coincide with the status of a given filter.

Figure 7:
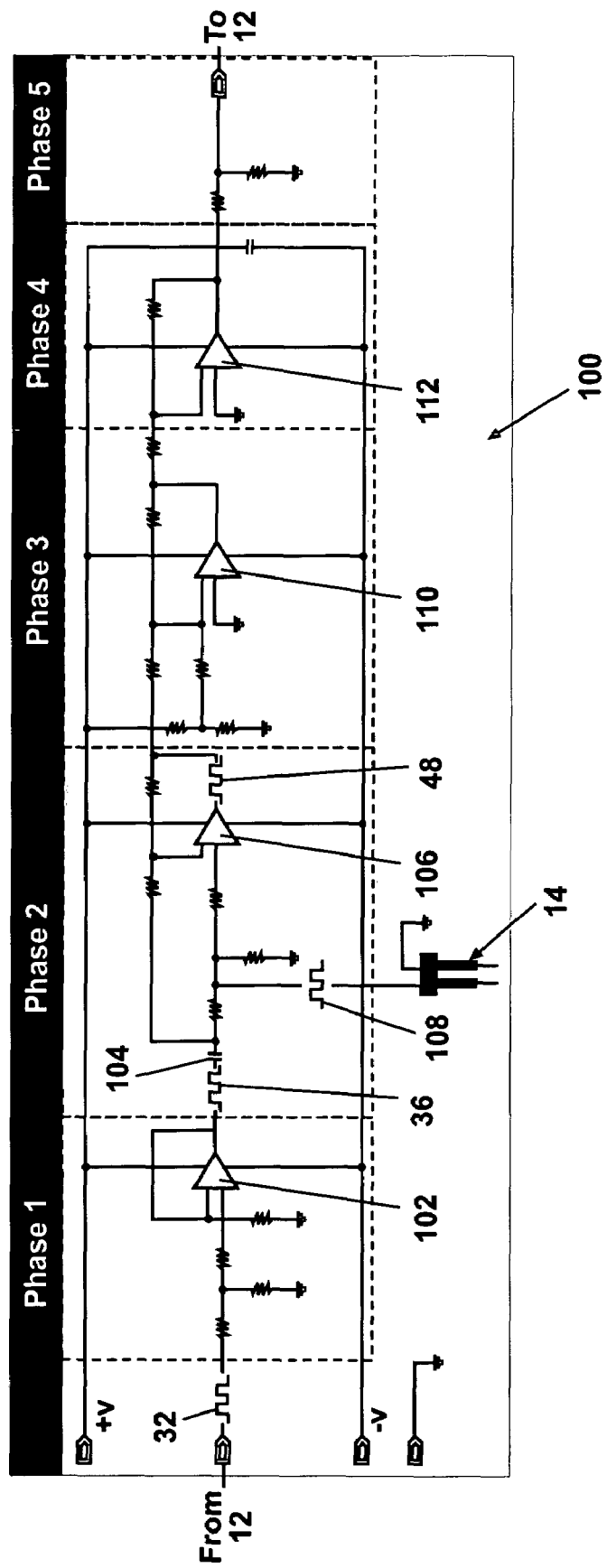
FIG. 7. is an exemplary circuit diagram of a water monitoring circuit according to the invention.

An exemplary conductivity sensor circuit 100 is shown in FIG. 7. It can be seen that the circuit 100 provides multiple amplifiers that sequentially act on the original square wave signal 32 generated by the microprocessor 12. Conceptually, it is helpful to think of the circuit 100 in terms of phases.

In phase 1, the circuit 100 uses an amplifier 102 that takes and converts the original square wave signal 32 to the excite signal 36. The output of phase 1 has no DC offset and the signal is inverted. In phase 2, the excite signal 36 is passed through a capacitor 104, sent through a voltage divider, and then to the probe 14. The probe signal 108, modified by the water and subtracted from the excite signal 36, goes to the amplifier 106 where the difference between the probe signal and the excite signals is amplified, inverted, and outputted with no DC offset as the raw final signal 48.

Phase 3 adds a DC offset back to the raw final signal 48 to start preparing it for the input into the microprocessor 12 and inverts the signal again at amplifier 110. Phase 4 is an optional phase to provide a buffer so that a later voltage divider does not affect previous stages, and to invert the raw final signal 48 one last time at amplifier 112 so that it is in phase with the excite signal 36. Phase 5 is a voltage divider to ensure that the highest value of the final signal will not exceed 3.3 volts for the input of the microprocessor 12.

Figure 8:
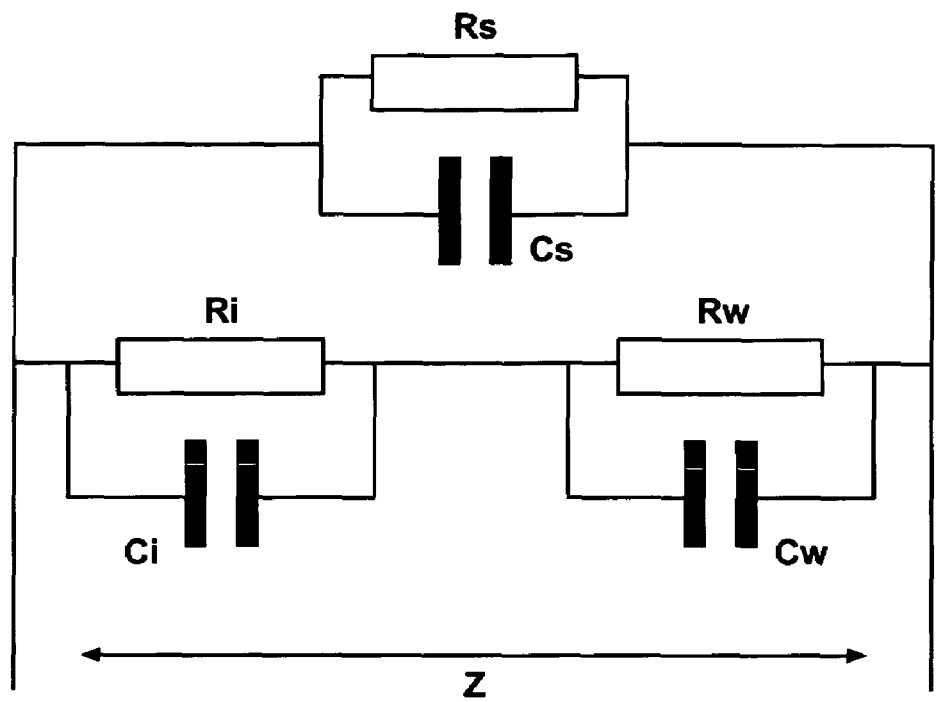
FIG. 8. is schematic diagram showing the equivalent electrical circuit of two electrodes in the water.
Figure 9:
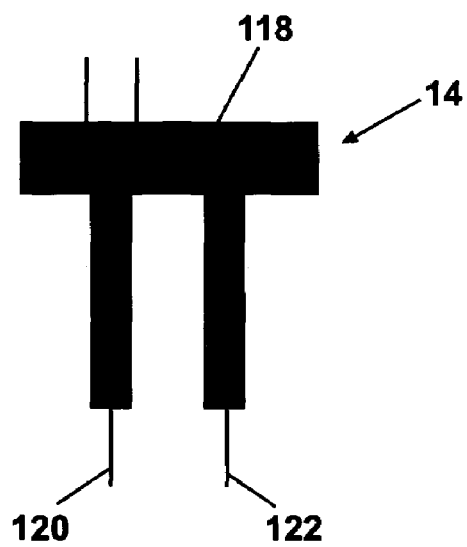
FIG. 9 is a diagram showing the geometry of a probe according to the invention.

FIG. 9 shows an exemplary configuration of the probe 14. The probe is preferably molded into a plastic holder 118 with two electrodes 120, 122. The physical effects that give impedance between the two electrodes 120, 122 in water can be modeled with the electrical equivalent circuit shown in FIG. 8. The equivalent impedance Z comprises a parallel circuit of water resistance $R_w$ and water capacitance $C_w$ in series with a parallel circuit of resistance $R_l$ and capacitance $C_l$, and stray resistance $R_s$ (the resistance of conductive water paths) in parallel with stray capacitance $C_s$ (the stray capacitance of electrical connections).

Water resistance and water capacitance depend on water electrical properties and geometry of electrodes and is determined by $$R_w = \frac{K}{\sigma} \text{ and}$$

$$C_w = \frac{\varepsilon_0 \varepsilon_r}{K}$$

where,
σ is the electrolytic conductivity of water, measured in siemens per meter [S/m];
$\varepsilon_r$ the relative permeability of water,
$\varepsilon_0$ the permeability of empty space, and
K the cell constant, measured in $m^{-1}$, which expresses geometry of electrodes, From these equations it is clear that water conductivity can be influenced by electrolytic conductivity and a cell constant K that is a design variable. The meaning of K is clear for the simplest electrode geometry, i.e., parallel plates of area S [$m^2$] and placed at distance d [m], where d<<sqrt (S). Thus:

K=d/S

But for electrodes comprising two parallel cylinders of length L and radius r, with axes spaced from each other at distance D, such as in the present configuration of the probe 14, $$K = \frac{\ln(D/r)}{\pi L}$$

The electrodes must be made of conducting material, inert with respect to expected water impurities (and, in addition, to acids or bases if a container maintenance is considered). Preferably, the electrodes are stainless and have a standard reduction potential as high as possible (in order to avoid discharge reactions). For this reason, copper (brass or bronze) and aluminium alloys are less favorable. In addition, electrode material should be food compatible where the steam to be generated comes into food contact. Nickel-based alloys (e.g., standard stainless steels) should be avoided because nickel is recognized as being potentially carcinogenic. Noble transition metals such as gold or platinum are acceptable. Cost may dictate other metals plated with noble metal, but integrity and continuity of plating must be achieved for the complete life of the sensor (zones where plating is scratched act as fast-corrosion sites because of galvanic cell effects). A preferred material for the electrodes is stainless steels AISI 316 L.

Figure 10:
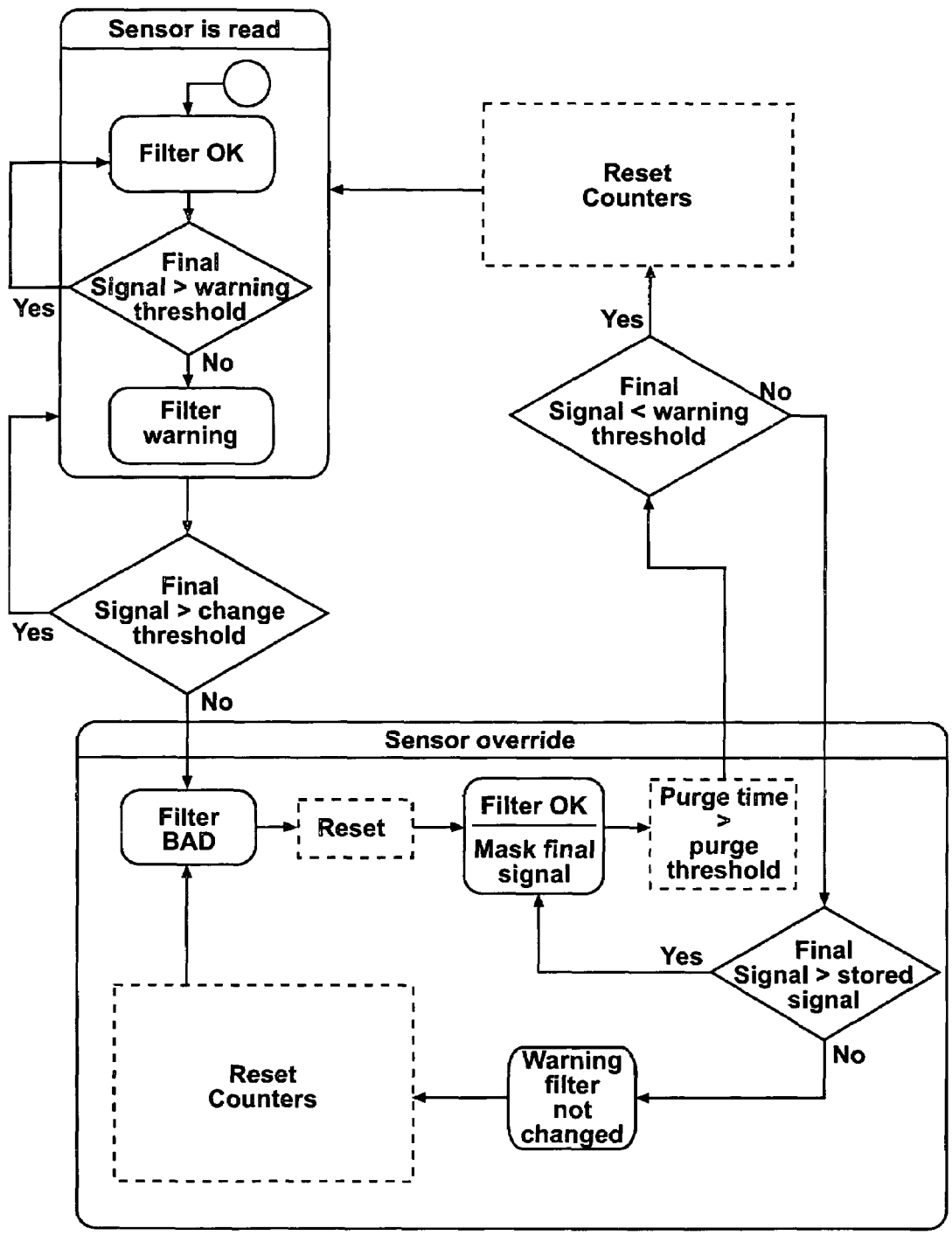
FIG. 10 is a block diagram showing a purge cycle.

Once the filter has been changed, there is a need to "reset" the system to recover an accurate indication. A finite time is required to drain the water from the tank (if that is the water source), to decrease the overall ion content, and to let the filter settle in order for the system to read the correct value. A "purge" cycle can be run manually or automatically according to the flow chart in FIG. 10. During a purge, the display 60 will show a good filter indication, regardless of the conductivity reading from the probe 14 until a predetermined time when the existing water prior to filter replacement will be considered to have been purged. The display 60 can be of the type shown in FIGS. 3-5 where the output is based solely on threshold values, or it can be a bar graph showing incremental values of conductivity relative to the thresholds, or any other display sufficient to show the condition of the filter.

While the invention has been specifically described in connection with certain specific embodiments thereof, it is to be understood that this is by way of illustration and not of limitation, and the scope of the appended claims should be construed as broadly as the prior art will permit.

What is claimed is:

1. A fluid conductivity monitoring circuit for determining the status of a filter disposed a flow of fluid, the circuit comprising:
    a microprocessor that generates an input signal and stores at least two threshold levels of conductivity,
    a probe, adapted to be positioned in the fluid flow downstream from the filter, that receives the input signal and returns an output signal, and
    a conductivity sensor circuit intermediate the microprocessor and the probe that compares the output signal to a comparison output signal and sends to the microprocessor a final signal indicative of the conductivity of the water, whereby when the probe is positioned in the fluid flow, the microprocessor can assess the status of the filter based on a comparison of the final signal to the threshold levels.

2. The fluid conductivity monitoring circuit of claim 1 further comprising a display connected to the microprocessor to show the status of the filter.

3. The water conductivity monitoring circuit of claim 1 wherein one of the at least two threshold levels indicates a need to change the filter.

4. The fluid conductivity monitoring circuit of claim 3 wherein a warning threshold is set at a conductivity of about 50 µS/cm, and a change threshold is set at about 100 µS/cm.

5. The water conductivity monitoring circuit of claim 1 wherein the reference signal is a pulsed wave.

6. The fluid conductivity monitoring circuit of claim 5 wherein the conductivity sensor circuit includes means to convert the reference signal to an excite signal to be sent to the probe.

7. The fluid conductivity monitoring circuit of claim 1 wherein the conductivity sensor circuit includes means to convert the reference signal to an excite signal to be sent to the probe.

8. The fluid conductivity monitoring circuit of claim 1 wherein the reference signal is in a range of 1-10 volts.

9. The fluid conductivity monitoring circuit of claim 1 wherein the probe has two electrodes, one of which is connected to ground.

10. The fluid conductivity monitoring circuit of claim 1 further including means to purge the water flow after changing the filter wherein the output signal is overridden for a predetermined time.

11. The fluid conductivity monitoring circuit of claim 1 wherein the fluid is water.

12. The fluid conductivity monitoring circuit of claim 1 disposed in a steam generating oven.

13. The fluid conductivity monitoring circuit of claim 1 wherein the microprocessor stores multiple threshold levels to determine a gradient representative of filter status.

14. The fluid conductivity monitoring circuit of claim 1 wherein the probe comprises two electrodes formed of conductive material that is substantially inert to fluid impurities.

* * * * *